United States Patent
Meyer et al.

(10) Patent No.: US 8,663,659 B2
(45) Date of Patent: Mar. 4, 2014

(54) ORALLY ADMINISTRABLE FILMS

(75) Inventors: Stephan Meyer, Genève (CH); Greg Slominski, Elmwood, NE (US); Christopher Edward Fankhauser, Eagle, NE (US)

(73) Assignee: Novartis AG, Basel (CH)

(*) Notice: Subject to any disclaimer, the term of this patent is extended or adjusted under 35 U.S.C. 154(b) by 594 days.

(21) Appl. No.: 12/529,659

(22) PCT Filed: Mar. 6, 2008

(86) PCT No.: PCT/US2008/002985
§ 371 (c)(1),
(2), (4) Date: Nov. 5, 2009

(87) PCT Pub. No.: WO2008/112124
PCT Pub. Date: Sep. 18, 2008

(65) Prior Publication Data
US 2010/0063110 A1   Mar. 11, 2010

Related U.S. Application Data

(60) Provisional application No. 60/893,419, filed on Mar. 7, 2007.

(51) Int. Cl.
*A61K 9/00* (2006.01)
*A61K 31/465* (2006.01)
*A61P 43/00* (2006.01)

(52) U.S. Cl.
USPC .......................................... 424/400; 514/343

(58) Field of Classification Search
None
See application file for complete search history.

(56) References Cited

U.S. PATENT DOCUMENTS

| 6,923,981 B2 * | 8/2005 | Leung et al. .................. 424/439 |
| 2003/0194420 A1 | 10/2003 | Holl |
| 2006/0084656 A1 * | 4/2006 | Ziegler et al. ................. 514/249 |
| 2006/0198873 A1 * | 9/2006 | Chan et al. .................... 424/443 |

FOREIGN PATENT DOCUMENTS

| EP | 1430896 | 6/2002 |
| JP | 2005247876 | 5/1998 |
| JP | 200551772 | 8/2003 |
| JP | 2006528636 | 2/2005 |
| WO | WO9600072 | 1/1996 |
| WO | WO0180837 | 11/2001 |
| WO | WO02/085119 | 10/2002 |
| WO | WO2004054551 | 7/2004 |
| WO | WO2006063189 | 6/2006 |

OTHER PUBLICATIONS

Bottenberg et al. (J. Pharm. Pharmacol. 1991, 43:457-464).*

* cited by examiner

*Primary Examiner* — David J Blanchard
*Assistant Examiner* — Garen Gotfredson
(74) *Attorney, Agent, or Firm* — Larson & Anderson, LLC

(57) ABSTRACT

The invention relates to oral disintegrable films, which are mucoadhesive, which completely disintegrate in the mouth of a consumer within 1 to 10 minutes, and which include an alkaline substance and optionally a pharmaceutically active substance.

17 Claims, No Drawings

ORALLY ADMINISTRABLE FILMS

The invention relates to oral disintegrable films, which are edible and optionally include pharmaceutically active substances. Especially, The invention relates to oral disintegrable films comprising an alkaline substance. More especially, the invention relates to oral disintegrable films which comprise an alkaline substance, which completely disintegrate in the mouth of a consumer within 1 to 10 minutes, preferably within 2 to 6 minutes, and which adhere to the buccal mucosa.

Thus, a preferred embodiment of the invention concerns oral disintegrable films that do not immediately dissolve in the mouth, e.g. within 1-10 seconds, but require a longer period of time for disintegration, e.g. 1 to 10 minutes, and adhere well to the buccal mucosa over that period of time. There may be various reasons to strive for such more slowly disintegrating oral films, e.g. allowing a pharmaceutically active substance to be effectively absorbed by the buccal mucosa, or e.g. to obtain a longer neutralizing effect by the alkaline substance on the saliva.

Slowly disintegrable oral films that are mucoadhesive are known in the art. It was found, however, that when adding an alkaline substance to the compositions of said slowly disintegrable oral films, the mucoadhesiveness of said films dramatically deteriorated. The need to include an alkaline substance to the composition may arise from various reasons, especially may it be used to increase the pH in the oral cavity after administration of the oral disintegrable film. This can be necessary e.g. to convert a pharmaceutically active substance in salt form into its unionized form (e.g. nicotine bitartrate to nicotine) and so to facilitate buccal absorption of said pharmaceutically active substance.

Thus, a goal of the present invention is to provide slowly disintegrable oral films that comprise an alkaline substance and nevertheless are mucoadhesive. It has been found, surprisingly, that when adding certain polymers to the composition, the films remains mucoadhesive despite the presence of an alkaline substance.

The invention therefore relates to an oral disintegrable film comprising
a layer, which comprises
(a) a film-forming agent,
(b) a polymer selected from the group consisting of croscarmellose sodium, corn starch, or a mixture thereof; and
(c) an alkaline substance.

A said oral disintegrable film, without including any further pharmaceutically active substance, may be useful by adhering to the buccal mucosa and e.g. neutralizing the saliva over several minutes, e.g. after eating acidic food like fruit (e.g. apples), or after eating food containing sugars which are broken down into acids by bacteria in the mouth. As said acids may cause dental erosion, it is beneficial to neutralize the acids taken up or formed with an alkaline substance-comprising oral disintegrable film.

Preferably, the oral disintegrable films according to the invention in addition comprise at least one pharmaceutically active substance (d).

A pharmaceutically active substance (d) may be any orally administrable pharmaceutically active substance, be it intended for absorption e.g. in the gastro-intestinal tract or via the buccal mucosa. Preferred are pharmaceutically active substances absorbed via the buccal mucosa, e.g. buprenorphine, nitroglycerin or nicotine. As can be seen from the mention of nicotine, the term "pharmaceutically active substance" is to be understood broadly so as to also include physiologically active substances which are intended to be orally administered.

In a particular embodiment of the invention, the pharmaceutically active substance (d) is prone to chemically react with the alkaline substance (c) and is therefore separated from the latter—within said oral disintegrable film—so as to avoid any premature chemical reaction before oral administration. "Separation" between (d) and (c) means that both components are hindered to chemically react with each other within the oral disintegrable film before administration and can be accomplished in many different ways, e.g. by physical separation in a two-layer film.

The pharmaceutically active substance (d) preferably is a nicotine active. A nicotine active is e.g. the free nicotine base, a nicotine salt, a nicotine complex, or mixtures thereof. Preferred are nicotine salts, in particular nicotine bitartrate.

A film-forming agent (a) is e.g. cellulose, cellulose ether derivatives, polyalkylene oxides, polyalkylene glycols, polyalkylene glycol copolymers, acrylic acid polymers, acrylic acid copolymers, methacrylic acid polymers, methacrylic acid copolymers, polyacrylamides, pullulan, polyvinyl pyrrolidone, polyvinyl alcohol, polyvinyl alcohol copolymers, carboxyvinyl polymers, modified starch, amylose, high amylose starch, hydroxypropylated high amylose starch, dextrin, pectin, chitin, chitosan, levan, elsinan, collagen, gelatin, zein, gluten, soy protein isolate, whey protein isolate, casein, synthetically or naturally occurring gums, carrageenan, alginic acid, salts of alginic acid, or mixtures thereof.

Preferred film-forming agents (a) are cellulose, hydroxypropylmethyl cellulose, hydroxyethyl cellulose, hydroxypropyl cellulose, polyethylene oxide, polypropylene oxide, polyethylene glycol, polypropylene glycol, acrylic acid polymers, acrylic acid copolymers, methacrylic acid polymers, methacrylic acid copolymers, polyacrylamides, pullulan, polyvinyl pyrrolidone, polyvinyl alcohol, carboxyvinyl polymers, modified starch, amylose, high amylose starch, hydroxypropylated high amylose starch, dextrin, pectin, chitin, chitosan, levan, elsinan, collagen, gelatin, zein, gluten, soy protein isolate, whey protein isolate, casein, xanthan gum, tragacanth gum, guar gum, acacia gum, arabic gum, carrageenan, alginic acid, salts of alginic acid, and mixtures thereof.

In particular preferred film-forming agents (a) are cellulose, hydroxypropylmethyl cellulose, hydroxyethyl cellulose, hydroxypropyl cellulose, polyethylene oxide, polyethylene glycol, polyacrylamides, pullulan, polyvinyl pyrrolidone, polyvinyl alcohol, modified starch, amylose, high amylose starch, hydroxypropylated high amylose starch, dextrin, pectin, chitin, collagen, gelatin, zein, gluten, soy protein isolate, whey protein isolate, casein, xanthan gum, tragacanth gum, guar gum, acacia gum, arabic gum, carrageenan, alginic acid, salts of alginic acid, and mixtures thereof.

Cellulose ether derivatives are e.g. hydroxypropylmethyl cellulose, hydroxyethyl cellulose, hydroxypropyl cellulose, hydroxyethylmethyl cellulose or methyl cellulose.

Preferably, the film-forming agent (a) is water-soluble.

Preferred as polymer (b) is croscarmellose sodium. Corn starch is synonymous to maize starch.

The alkaline substance (c) is e.g. sodium carbonate, potassium carbonate, sodium bicarbonate, potassium bicarbonate, sodium hydroxide, potassium hydroxide, or any mixture thereof.

Preferred alkaline substances (c) are sodium carbonate, potassium carbonate, sodium hydroxide, potassium hydroxide, or any mixture thereof.

A particular embodiment of the invention is characterized by those oral disintegrable films which comprise, as film-forming agent (a),
(a1) a water-soluble film-forming polymer and
(a2) 0.1-20% by weight of a hydrocolloid/biopolymer gum.

Of the latter, those oral disintegrable films are preferred, which comprise 0.1 to 15%—more preferably 0.3 to 5% and in particular 0.5 to 3%—by weight of the hydrocolloid/biopolymer gum (a2).

Water-soluble film-forming polymers (a1) are e.g. cellulose, cellulose ether derivatives, polyalkylene oxides, polyalkylene glycols, polyalkylene glycol copolymers, acrylic acid polymers, acrylic acid copolymers, methacrylic acid polymers, methacrylic acid copolymers, polyacrylamides, pullulan, polyvinyl pyrrolidone, polyvinyl alcohol, polyvinyl alcohol copolymers, carboxyvinyl polymers, or mixtures thereof.

Preferred water-soluble film-forming polymers (a1) are cellulose, cellulose ether derivatives, polyalkylene glycol copolymers, polyvinyl alcohol, polyvinyl alcohol copolymers, or mixtures thereof.

More preferred water-soluble film-forming polymers (a1) are hydroxypropylmethyl cellulose, hydroxyethyl cellulose, hydroxypropyl cellulose, polyvinyl alcohol, or mixtures thereof. In particular, the water-soluble film-forming polymer (a1) is hydroxypropylmethyl cellulose.

A hydrocolloid/biopolymer gum (a2) is e.g. a synthetically or naturally occurring gum, carrageenan, alginic acid, a salt of alginic acid, or mixtures thereof.

Preferably, the hydrocolloid/biopolymer gum (a2) is xanthan gum, tragacanth gum, guar gum, acacia gum, arabic gum, or mixtures thereof. In particular, the hydrocolloid/biopolymer gum (a2) is xanthan gum.

Other components that may be present in the oral disintegrable films of the invention are e.g. plasticizers. As plasticizers, there come into consideration, for example, polyalcohols, e.g. glycerol, polyethylene glycol, ethylene glycol or propylene glycol; glycerol monoesters with fatty acids, e.g. n-octanoic acid or oleic acid; sorbitol, polysorbate 80 [=polyoxyethylene (20) sorbitan monooleate], triethyl citrate, acetyl triethyl citrate, tributyl citrate or diethyl phthalate.

Preferred as plasticizers are glycerol, polyethylene glycol, ethylene glycol, propylene glycol, triethyl citrate, or any mixture thereof; and in particular glycerol.

The plasticizer is typically present in amounts ranging from 0.1 to 15—preferably from 1 to 8 and even more preferably from 1.5 to 7—weight-% of the final edible film (dry mass). In a particular embodiment of the invention, the plasticizer (B) is glycerol and is present in amounts ranging from 1 to 12—preferably 1 to 7, and more preferably 1.5 to 6—weight-% of the film (dry mass).

Moreover, the edible films of the invention optionally include usual auxiliaries as known in the art, such as, for example, flavors, sweeteners, antioxidants, stabilizers, coloring agents, solubilizing agents or preservatives.

In general, those oral disintegrable films are preferred, which adhere to the buccal mucosa.

In general, those oral disintegrable films are preferred, which completely disintegrate in the mouth of a consumer within 1 to 10—preferably 2 to 6 and in particular 3 to 4—minutes.

"Completely disintegrating" means that no macroscopic residue is left in the mouth of a patient. From a practical standpoint, the oral disintegrable films of the invention completely dissolve in the mouth within the time periods indicated, with a proviso to be made from a strict scientific standpoint, namely that, obviously, components of the film that are not soluble in the saliva will not dissolve but rather be dispersed and remain in the solid state.

The oral disintegrable films according to the invention may have one or more layers and typically have a thickness of from 5-3000—preferably 10-1000, more preferably 20-500 and in particular 30-300—micrometers. In another embodiment, they have a thickness of 5 to 250 micrometers.

The oral disintegrable films according to the invention are not limited to any particular size, preferably they are rectangular, square or round, in particular rectangular or square, typically with an area of 2-20—preferably 2-12, more preferably 3-12 and especially 4-7, square centimeters, typically—if rectangular or square—with side lengths of 0.5-3 cm and 2-20 cm—preferably 1-3 cm and 2-5 cm—, respectively. A particularly preferred dimension is 2.2 cm×2.2 cm (square).

The beneficial properties of the oral disintegrable films of the invention can be demonstrated e.g. by the following tests:
(a) Disintegration of the films: The disintegration time of the films is measured e.g. in vitro as well as in clinical tests in the mouth of patients.
(b) Mucoadhesiveness of the films: The mucoadhesiveness of the films is measured e.g. with a tensile strength tester: The films are applied with artificial saliva on pig excised mucosa and the tensile strength (=maximum force of detachment in mN) is measured until the film is torn out from the mucosa. For example, the film of Example 1 shows a high mucoadhesion of 838±119 mN, which is the same magnitude of mucoadhesion as a comparative film that is identical to that of Example 1 but lacks the presence of the alkaline substance sodium carbonate. Thus, the presence of additional sodium carbonate in the film of Example 1, surprisingly, does not lower its mucoadhesion.
(c) Stability tests: The chemical and physical stability of the films is confirmed, e.g. in three months or one year studies under strictly controlled conditions (temperature/humidity).

The oral disintegrable films of the invention can be manufactured in a manner known per se, for example as outlined in the following examples.

The following examples illustrate the invention.

EXAMPLE 1

Oral Disintegrable Film Containing Sodium Carbonate and Croscarmellose (for pH Regulation in the Oral Cavity) [="Layer 1" of a Two-Layer Oral Disintegrable Film Containing Sodium Carbonate and Nicotine Bitartrate]

| Ingredients | Amount (mg) |
| --- | --- |
| Hydroxypropylmethyl cellulose ("HPMC") | 30.00 |
| Croscarmellose sodium | 6.00 |
| Glycerol | 3.00 |
| Xantham gum | 1.00 |
| Sodium carbonate | 8.00 |
| Menthol | 1.50 |
| Acesulfam K | 0.50 |
| Mint flavor | 1.00 |
| Total dry mass | 51.00 |
| Water | 220.00 |
| Ethanol 96% | 140.00 |
| Total wet mass | 411.00 |

Process: Sodium carbonate, acesulfam K and menthol are dissolved in water. Glycerol and ethanol are then added (sodium carbonate precipitation). HPMC, croscarmellose sodium and xanthan gum are added slowly under strong stirring. Slow stirring is kept until homogenization of the viscous mixture. The viscous mixture is spread, as a layer of uniform thickness, on a plate and dried in an oven (="Layer 1").

For obtaining finished oral disintegrable films for pH regulation in the oral cavity, said "Layer 1" is further cut into, for example, rectangles of 2 cm×3 cm, and the latter are packed individually in pouches.

EXAMPLE 2

Two-Layer Oral Disintegrable Film Containing 3.067 Mg of Nicotine Bitartrate (=1 mg Nicotine Base), Sodium Carbonate and Croscarmellose Sodium (A) Preparation of a film layer containing nicotine bitartrate (with croscarmellose)

| Ingredients | Amount (mg) |
| --- | --- |
| Hydroxypropylmethyl cellulose ("HPMC") | 30.00 |
| Croscarmellose sodium | 6.00 |
| Glycerol | 3.00 |
| Xantham gum | 1.00 |
| Nicotine bitartrate (=1 mg nicotine base) | 3.07 |
| Menthol | 1.50 |
| Acesulfam K | 0.50 |
| Mint flavor | 1.00 |
| Total dry mass | 46.07 |
| Water | 220.00 |
| Ethanol 96% | 140.00 |
| Total wet mass | 406.07 |

Process: Nicotine bitartrate, acesulfam K and menthol are dissolved in the water-ethanol mix. Glycerol and liquid mint flavor is then added. HPMC, croscarmellose sodium and xanthan gum are added slowly under strong stirring. Slow stirring is kept until homogenization of the viscous mixture. The viscous mixture is spread, as a layer of uniform thickness, on a plate and dried in an oven.

(A1) Preparation of a film layer containing nicotine bitartrate (without croscarmellose):

| Ingredients | Amount (mg) |
| --- | --- |
| Hydroxypropylmethyl cellulose ("HPMC") | 30.00 |
| Glycerol | 4.00 |
| Xantham gum | 3.00 |
| Nicotine bitartrate (=1 mg nicotine base) | 3.07 |
| Menthol | 1.50 |
| Acesulfam K | 0.50 |
| Mint flavor | 1.00 |
| Total dry mass | 43.07 |
| Water | 240.00 |
| Ethanol 96% | 250.00 |
| Total wet mass | 533.07 |

Process: Nicotine bitartrate, acesulfam K and menthol are dissolved in the water-ethanol mix. Glycerol and liquid mint flavor are then added. HPMC and xanthan gum are added slowly under strong stirring. Slow stirring is kept until homogenization of the viscous mixture. The viscous mixture is spread, as a layer of uniform thickness, on a plate and dried in an oven.

(B) Combination of "Layer 1" (see Example 1) with layer (A) or (A1), respectively: Both layers are combined by first nebulizing "Layer 1" with an ethanol spray and then applying a weak pressure on layer (A) [or (A1), respectively] against "Layer 1". The resulting double-layer is dried and cut into two-layer oral disintegrable films of a defined size (e.g. rectangles of 2 cm×3 cm), and the latter are packed individually in pouches.

EXAMPLE 3

Oral Disintegrable Film Containing Sodium Carbonate and Corn Starch (for pH Regulation in the Oral Cavity)

| Ingredients | Amount (mg) |
| --- | --- |
| HPMC | 25.00 |
| Corn starch | 15.00 |
| Glycerol | 3.00 |
| Xantham gum | 1.00 |
| Sodium carbonate | 8.00 |
| Menthol | 1.50 |
| Acesulfam K | 0.50 |
| Mint flavor | 1.00 |
| Total dry mass | 55.00 |
| Water | 200.00 |
| Ethanol 96% | 120.00 |
| Total wet mass | 375.00 |

Process: Sodium carbonate, acesulfam K and menthol are dissolved in water. Glycerol, liquid mint flavor and ethanol are added (sodium carbonate precipitation). HPMC, corn starch and xanthan gum are added slowly under strong stirring. Slow stirring is kept until homogenization of the viscous mixture. The viscous mixture is spread, as a layer of uniform thickness, on a plate and dried in an oven. Finally, said layer is cut into, for example, rectangles of 2 cm×3 cm, and the latter are packed individually in pouches.

The invention claimed is:
1. An oral disintegrable film comprising a layer, which layer comprises
   (a) a film-forming agent,
   (b) croscarmellose sodium or a mixture of croscarmellose sodium and corn starch; and
   (c) an alkaline substance.
2. The oral disintegrable film according to claim 1, which film in addition comprises a pharmaceutically active substance.
3. The oral disintegrable film according to claim 2, wherein the pharmaceutically active substance is prone to chemically react with the alkaline substance and the pharmaceutically active substance is separated from the alkaline substance thereby avoiding any premature chemical reaction before oral application.
4. The oral disintegrable film according to claim 1, wherein the film-forming agent is selected from the group consisting of cellulose, cellulose ether derivatives, polyalkylene oxides, polyalkylene glycols, polyalkylene glycol copolymers, acrylic acid polymers, acrylic acid copolymers, methacrylic acid polymers, methacrylic acid copolymers, polyacrylamides, pullulan, polyvinyl pyrrolidone, polyvinyl alcohol, polyvinyl alcohol copolymers, carboxyvinyl polymers, modified starch, amylose, high amylose starch, hydroxypropylated high amylose starch, dextrin, pectin, chitin, chitosan, levan, elsinan, collagen, gelatin, zein, gluten, soy protein isolate, whey protein isolate, casein, synthetically or naturally occurring gums, carrageanan, alginic acid, salts of alginic acid, and any mixture thereof.

5. The oral disintegrable film according to claim 1, wherein the alkaline substance is selected from the group consisting of sodium carbonate, potassium carbonate, sodium bicarbonate, potassium bicarbonate, sodium hydroxide, potassium hydroxide, and any mixture thereof.

6. The oral disintegrable film according to claim 2, wherein the pharmaceutically active substance is a nicotine active.

7. The oral disintegrable film according to claim 1 wherein the film-forming agent is
   a water-soluble film-forming polymer and
   0.1-20% by weight of the film of a hydrocolloid/biopolymer gum.

8. The oral disintegrable film according to claim 7, which film comprises 0.3 to 5% by weight of the hydrocolloid/biopolymer gum (a2).

9. The oral disintegrable film according to claim 1, wherein the film adheres to the buccal mucosa.

10. The oral disintegrable film according to claim 1, wherein the film completely disintegrates in the mouth within 1 to 10 minutes.

11. The oral disintegrable film according to claim 1, wherein the film has a thickness of 5 to 250 micrometers.

12. The oral disintegrable film according to claim 7, wherein the pharmaceutically active substance is a nicotine active.

13. The oral disintegrable film of claim 12, wherein the nicotine active is a nicotine salt.

14. The oral disintegrable film of claim 13, wherein the nicotine salt is nicotine bitartrate.

15. The oral disintegrable film according to claim 7, wherein the water-soluble film-forming polymer is hydroxypropylmethyl cellulose.

16. The oral disintegrable film according to claim 7, wherein the hydrocolloid/biopolymer gum is selected from the group consisting of carrageanan, alginic acid, salts of alginic acid, and mixtures thereof.

17. The oral disintegrable film according to claim 7, wherein the hydrocolloid/biopolymer gum is xanthan gum.

* * * * *